(12) United States Patent
Gentalen

(10) Patent No.: US 10,209,217 B2
(45) Date of Patent: Feb. 19, 2019

(54) DEVICES AND METHODS FOR SAMPLE CHARACTERIZATION

(71) Applicant: Intabio, Inc., Fremont, CA (US)

(72) Inventor: Erik Gentalen, Fremont, CA (US)

(73) Assignee: Intabio, Inc., Fremont, CA (US)

( * ) Notice: Subject to any disclaimer, the term of this patent is extended or adjusted under 35 U.S.C. 154(b) by 0 days.

(21) Appl. No.: 15/709,158

(22) Filed: Sep. 19, 2017

(65) Prior Publication Data
US 2018/0003674 A1 Jan. 4, 2018

Related U.S. Application Data

(63) Continuation of application No. 15/363,908, filed on Nov. 29, 2016.

(60) Provisional application No. 62/260,944, filed on Nov. 30, 2015, provisional application No. 62/338,074, filed on May 18, 2016.

(51) Int. Cl.
*G01N 27/447* (2006.01)
*H01J 49/04* (2006.01)
*B01L 3/00* (2006.01)
*B01L 3/02* (2006.01)
*H01J 49/16* (2006.01)

(52) U.S. Cl.
CPC .. *G01N 27/44791* (2013.01); *B01L 3/502715* (2013.01); *H01J 49/04* (2013.01); *B01L 3/0268* (2013.01); *B01L 2200/143* (2013.01); *B01L 2300/0654* (2013.01); *B01L 2300/0816* (2013.01); *B01L 2300/0861* (2013.01); *B01L 2400/0421* (2013.01); *G01N 2223/40* (2013.01); *G01N 2223/50* (2013.01); *G01N 2550/00* (2013.01); *H01J 49/167* (2013.01)

(58) Field of Classification Search
CPC .......................... C12Q 2565/629; B01L 9/527
See application file for complete search history.

(56) References Cited

U.S. PATENT DOCUMENTS

| 5,259,939 A | 11/1993 | Chen |
| 5,395,502 A | 3/1995 | Pawliszyn |
| 5,468,359 A | 11/1995 | Pawliszyn |

(Continued)

FOREIGN PATENT DOCUMENTS

| AT | 548347 T | 3/2012 |
| DE | 05705627 T1 | 5/2007 |

(Continued)

OTHER PUBLICATIONS

Yang et al. "Capillary isoelectric focusing-electrospray ionization mass spectrometry for transferrin glycoforms analysis". Analytical Biochemistry 243, 1996, p. 140-149. (Year: 1996).*

(Continued)

*Primary Examiner* — Krishnan S Menon
*Assistant Examiner* — Ryan B Huang
(74) *Attorney, Agent, or Firm* — Wilson Sonsini Goodrich & Rosati

(57) ABSTRACT

Devices and methods for characterization of analyte mixtures are provided. Some methods described herein include performing enrichment steps on a device before expelling enriched analyte fractions from the device for subsequent analysis. Also included are devices for performing these enrichment steps.

23 Claims, 8 Drawing Sheets

(56) References Cited

U.S. PATENT DOCUMENTS

| | | | |
|---|---|---|---|
| 5,779,868 A | 7/1998 | Parce et al. | |
| 5,784,154 A | 7/1998 | Pawliszyn | |
| 5,800,690 A | 9/1998 | Chow et al. | |
| 5,842,787 A | 12/1998 | Kopf-Sill et al. | |
| 5,858,195 A | 1/1999 | Ramsey | |
| 5,876,675 A | 3/1999 | Kennedy | |
| 5,880,071 A | 3/1999 | Parce et al. | |
| 5,957,579 A | 9/1999 | Kopf-Sill et al. | |
| 5,958,203 A | 9/1999 | Parce et al. | |
| 5,965,001 A | 10/1999 | Chow et al. | |
| 5,972,187 A | 10/1999 | Parce et al. | |
| 5,985,121 A | 11/1999 | Wu et al. | |
| 6,001,229 A | 12/1999 | Ramsey | |
| 6,010,607 A | 1/2000 | Ramsey | |
| 6,010,608 A | 1/2000 | Ramsey | |
| 6,033,546 A | 3/2000 | Ramsey | |
| 6,042,709 A | 3/2000 | Parce et al. | |
| 6,048,498 A | 4/2000 | Kennedy | |
| 6,080,295 A | 6/2000 | Parce et al. | |
| 6,110,343 A | 8/2000 | Ramsey et al. | |
| 6,149,787 A | 11/2000 | Chow et al. | |
| 6,167,910 B1 | 1/2001 | Chow | |
| 6,186,660 B1 | 2/2001 | Kopf-Sill et al. | |
| 6,231,737 B1 | 5/2001 | Ramsey et al. | |
| 6,287,520 B1 | 9/2001 | Parce et al. | |
| 6,321,791 B1 | 11/2001 | Chow | |
| 6,413,401 B1 | 7/2002 | Chow et al. | |
| 6,430,512 B1 | 8/2002 | Gallagher | |
| 6,482,364 B2 | 11/2002 | Parce et al. | |
| 6,494,230 B2 | 12/2002 | Chow et al. | |
| 6,517,234 B1 | 2/2003 | Kopf-Sill et al. | |
| 6,547,942 B1 | 4/2003 | Parce et al. | |
| 6,611,768 B2 | 8/2003 | Gallagher | |
| 6,632,655 B1 | 10/2003 | Mehta et al. | |
| 6,803,568 B2 | 10/2004 | Bousse et al. | |
| 6,831,274 B2 | 12/2004 | Smith et al. | |
| 6,974,527 B2 | 12/2005 | Liu et al. | |
| 7,001,496 B2 | 2/2006 | Parce et al. | |
| 7,022,214 B2 | 4/2006 | Olech | |
| 7,166,202 B2 | 1/2007 | Bukshpan et al. | |
| 7,285,411 B1 | 10/2007 | Parce et al. | |
| 7,339,166 B2 | 3/2008 | Tang et al. | |
| 7,381,317 B2 | 6/2008 | Liu et al. | |
| 7,391,020 B2 | 6/2008 | Bousse et al. | |
| 7,425,700 B2 | 9/2008 | Stults et al. | |
| 7,426,442 B2 | 9/2008 | Gallagher | |
| 7,655,477 B1 | 2/2010 | Schneider et al. | |
| 7,825,375 B2 | 11/2010 | Sano | |
| 8,076,152 B2 | 12/2011 | Robotti | |
| 8,097,472 B2 | 1/2012 | Schneider et al. | |
| 8,260,561 B2 | 9/2012 | Gallagher | |
| 8,613,845 B2 | 12/2013 | Maxwell et al. | |
| 8,859,296 B2 | 10/2014 | Schneider et al. | |
| 8,940,232 B2 | 1/2015 | Roach et al. | |
| 9,006,648 B2 | 4/2015 | Ramsey et al. | |
| 9,159,537 B2 | 10/2015 | McGivney et al. | |
| 9,255,905 B1 | 2/2016 | Mellors et al. | |
| 9,347,440 B2 | 5/2016 | Lebl et al. | |
| 9,362,102 B2 | 6/2016 | Dovichi et al. | |
| 9,377,440 B2 | 6/2016 | Wu et al. | |
| 9,465,014 B2 | 10/2016 | Dovichi et al. | |
| 9,502,225 B2 | 11/2016 | Mellors et al. | |
| 9,606,082 B2 | 3/2017 | Mellors et al. | |
| 9,728,387 B2 | 8/2017 | Mellors et al. | |
| 9,778,223 B2 | 10/2017 | Schneider et al. | |
| 2002/0079220 A1 | 6/2002 | Pawliszyn | |
| 2002/0139751 A1* | 10/2002 | Zhang | B01J 20/28042 210/656 |
| 2004/0113068 A1* | 6/2004 | Bousse | B01L 3/0268 250/288 |
| 2005/0021799 A1 | 1/2005 | Imamura et al. | |
| 2008/0035484 A1* | 2/2008 | Wu | G01N 1/40 204/548 |
| 2008/0318334 A1* | 12/2008 | Robotti | G01N 30/6095 436/161 |
| 2009/0194419 A1 | 8/2009 | Huang et al. | |
| 2010/0116659 A1 | 5/2010 | Liu et al. | |
| 2010/0155243 A1 | 6/2010 | Schneider et al. | |
| 2010/0193702 A1* | 8/2010 | Li | H01J 49/107 250/424 |
| 2011/0072914 A1* | 3/2011 | Lebl | B01L 3/50273 73/864.11 |
| 2011/0243813 A1 | 10/2011 | Jackinsky et al. | |
| 2012/0080316 A1 | 4/2012 | Schneider et al. | |
| 2013/0140180 A1 | 6/2013 | Dovichi et al. | |
| 2013/0190212 A1 | 7/2013 | Handique et al. | |
| 2013/0280815 A1 | 10/2013 | Wu | |
| 2014/0360877 A1 | 12/2014 | Ramsey et al. | |
| 2015/0008130 A1 | 1/2015 | Schneider et al. | |
| 2015/0093757 A1 | 4/2015 | Gavin | |
| 2015/0340219 A1 | 11/2015 | Mellors et al. | |
| 2015/0362460 A1 | 12/2015 | Ferguson | |
| 2016/0370319 A1 | 12/2016 | Molho et al. | |
| 2017/0025263 A1 | 1/2017 | Mellors et al. | |
| 2017/0045527 A1 | 2/2017 | Muthusamy et al. | |
| 2017/0176386 A1 | 6/2017 | Gentalen | |
| 2017/0299549 A1 | 10/2017 | Schneider et al. | |
| 2017/0363575 A1 | 12/2017 | Huang | |

FOREIGN PATENT DOCUMENTS

| | | |
|---|---|---|
| EP | 1718960 B1 | 3/2012 |
| JP | 4900245 B2 | 3/2012 |
| WO | WO-2005072121 A2 | 8/2005 |
| WO | WO-2007055293 A1 | 5/2007 |
| WO | WO-2015048458 A2 | 4/2015 |
| WO | WO-2017012397 A1 | 1/2017 |
| WO | WO-2017/095813 | 6/2017 |
| WO | WO-2017095813 A1 | 6/2017 |
| WO | WO-2017123970 A1 | 7/2017 |

OTHER PUBLICATIONS

Shimura et al. (Anal. Chem. 2008, 80, p. 3818-3823) "Isoelectric focusing in a microfluidically defined electrophoresis channel" (Year: 2008).*

Yang et al. "Capillary Isoelectric Focusing—Electrospray Ionization Mass Spectrometry for Transferrin Glycoforms Analysis" (Anal. Biochem. 1996, 243, 140-149) (Year: 1996).*

Shimura et al. "Isoelectric Focusing in a Microfluidically Defined Electrophoresis Channel" (Anal. Chem. 2008, 80, p. 3818-3823) (Year: 2008).*

Zhang et al. "Microfabricated Devices for Capillary Electrophoresis-Electrospray Mass Spectrometry" (Anal. Chem. 1999, 71, 3258-3264) (Year: 1999).*

Týčová et al. Recent advances in CE-MS coupling: Instrumentation, methodology, and applications. Electrophoresis. Jan. 2017;38(1):115-134.

Baker, C. et al., "Online Coupling of Digital Microfluidic Devices with Mass Spectrometry Detection Using an Eductor with Electrospray Ionization", *Analytical Chemistry*, vol. 84, 2012, 6 pages.

Benz, C. et al., "Chip-Based Free-Flow Electrophoresis with Integrated Nanospray Mass-Spectrometry", *Angewandte Chemie International Edition*, vol. 54, 2015, 5 pages.

Cui, H. et al., "Isoelectric Focusing in a Poly(dimethylsiloxane) Microfluidic Chip", *Analytical Chemistry*, vol. 77, 2005, 7 pages.

Figeys, D. et al., "An Integrated Microfluidics-Tandem Mass Spectrometry System for Automated Protein Analysis", *Analytical Chemistry*, vol. 70, No. 18, Sep. 15, 1998, 7 pages.

Haselberg, R. et al., "Performance of a Sheathless Porous Tip Sprayer for Capillary Electrophoresis-Electrospray Ionization-Mass Spectrometry of Intact Proteins", *Journal of Chromatography A*, vol. 1217, 2010, 7 pages.

Hu, X. et al., "Fabrication of a Polystyrene Microfluidic Chip Coupled to Electrospray Ionization Mass Spectrometry for Protein Analysis", *Journal of Chromatography B*, vol. 990, 2015, 8 pages.

Jiang, Y. et al., "Integrated Plastic Microfluidic Devices with ESI-MS for Drug Screening and Residue Analysis", *Analytical Chemistry*, vol. 73, 2001, 6 pages.

(56) References Cited

OTHER PUBLICATIONS

Li, N. et al., "Evaluation of the iCE280 Analyzer as a Potential High-Throughput Tool for Formulation Development", *Journal of Pharmaceutical and Biomedical Analysis*, vol. 43, 2007, 11 pages.

Li, Y. et al., "Integration of Isoelectric Focusing with Parallel Sodium Dodecyl Sulfate Gel Electrophoresis for Multidimensional Protein Separations in a Plastic Microfluidic Network", *Analytical Chemistry*, vol. 76, 2004, 7 pages.

Mao, Q. et al., "Demonstration of Isoelectric Focusing on an Etched Quartz Chip with UV Absorption Imaging Detection", *Analyst*, vol. 124, 1999, 5 pages.

Marasco, C. et al., "Real-Time Cellular Exometabolome Analysis With a Microfluidic-Mass Spectrometry Platform", *PLOS One*, Feb. 27, 2015, 19 pages.

Mellors, J. et al., "Fully Integrated Glass Microfluidic Device for Performing High-Efficiency Capillary Electrophoresis and Electrospray Ionization Mass Spectrometry", *Analytical Chemistry*, vol. 80, 2008, 7 pages.

Nordman, N. et al., "Interfacing Microchip Isoelectric Focusing with On-chip Electrospray Ionization Mass Spectrometry", *Journal of Chromatography A*, vol. 1398, 2015, 6 pages.

Nordman, N., "Microchip Technology in Mass Spectrometry-Based Bioanalysis: Advances in the Analysis of Peptides, Proteins, and Pharmaceuticals", Academic Dissertation, University of Helsinki, Apr. 17, 2015, 144 pages.

Nordman, N. et al., "Rapid Biomolecule Analysis Using Two-Dimensional Electrophoresis-Electrospray Ionization Microchip", *15th International Conference on Miniaturized Systems for Chemistry and Life Science*, Oct. 2-6, 2011, Seattle, Washington, 3 pages.

Salas-Solano, O. et al., "Intercompany Study to Evaluate the Robustness of Capillary Isoelectric Focusing Technology for the Analysis of Monoclonal Antibodies", *Chromatographia*, vol. 73, 2011, 8 pages.

Shimura, K. et al., "Isoelectric Focusing in a Microfluidically Defined Electrophoresis Channel", *Analytical Chemistry*, vol. 80, 2008, 6 pages.

Sikanen, T. et al., "Intact Protein Separations With Inherently Biocompatible Ormocomp Separation Chip With Integrated Electrospray Ionization Emitter", *15th International Conference on Miniaturized Systems for Chemistry and Life Science*, Oct. 2-6, 2011, Seattle, Washington, 3 pages.

Sikanen, T. et al., "Microchip Capillary Electrophoresis-Electrospray Ionization-Mass Spectrometry of Intact Proteins Using Uncoated Ormocomp Microchips", *Analytica Chimica Acta*, vol. 711, 2012, 8 pages.

Sikanen, T. et al., "Microchip Technology in Mass Spectrometry", *Mass Spectrometry Reviews*, vol. 29, 2010, 41 pages.

Suzuki, S. et al., "High-speed Electrophoretic Analysis of 1-phenyl-3-methyl-5-pyrazolone Derivatives of Monosaccharides on a Quartz Microchip with Whole-Channel UV Detection", *Electrophoresis*, vol. 24, 2003, 6 pages.

Tan, W. et al., "Miniaturized Capillary Isoelectric Focusing in Plastic Microfluidic Devices", *Electrophoresis*, vol. 23, 2002, 8 pages.

Taylor, P., "Matrix Effects: The Achilles Heel of Quantitative High-Performance Liquid Chromatography-Electrospray-Tandem Mass Spectrometry", *Clinical Biochemistry*, vol. 38, 2005, 7 pages.

Vlčková, M. et al., "Pharmaceutical Applications of Isoelectric Focusing on Microchip With Imaged UV Detection", *Journal of Chromatography A*, vol. 1181, 2008, 8 pages.

Wakankar, A. et al., "Analytical Methods for Physicochemical Characterization of Antibody Drug Conjugates", *mAbs*, vol. 3, No. 2, Mar./Apr. 2011, 12 pages.

Wen, J. et al., "Microfabricated Isoelectric Focusing Device for Direct Electrospray Ionization-Mass Spectrometry", *Electrophoresis*, vol. 21, 2000, 7 pages.

Wu, J. et al., "Absorption Spectra and Multicapillary Imaging Detection for Capillary Isoelectric Focusing Using a Charge Coupled Device Camera", *Analyst*, vol. 120, May 1995, 5 pages.

Wu, J. et al., "Capillary Isoelectric Focusing with Whole Column Detection and a Membrane Sample Preparation System", *Analytica Chimica Acta*, vol. 383, 1999, 12 pages.

Wu, J. et al., "Protein Analysis by Isoelectric Focusing in a Capillary Array With an Absorption Imaging Detector", *Journal of Chromatography B*, vol. 669, 1995, 5 pages.

Zhang, B. et al., "Microfabricated Devices for Capillary Electrophoresis-Electrospray Mass Spectrometry", *Analytical Chemistry*, vol. 71, 1999, 7 pages.

Zhong, X, et al., "Flow-Through Microvial Facilitating Interface of Capillary Isoelectric Focusing and Electrospray Ionization Mass Spectrometry", *Analytical Chemistry*, vol. 83, 2011, 8 pages.

International Search Report and Written Opinion issued by the International Searching Authority for Application No. PCT/US16/64013, dated May 11, 2017, 20 pages.

Chen, et al. Comparison of ampholytes used for slab gel and capillary isoelectric focusing of recombinant tissue-type plasminogen activator glycoforms. J Chromatogr A. Sep. 13, 1996;744(1-2):279-84.

Dolník, V. Wall coating for capillary electrophoresis on microchips. Electrophoresis. Nov. 2004;25(21-22):3589-601.

Geiser, et al. Potential of formamide and N-methylformamide in nonaqueous capillary electrophoresis coupled to electrospray ionization mass spectrometry. Application to the analysis of beta-blockers. J Chromatogr A. Dec. 6, 2002;979(1-2):389-98.

Hjertén, Stellan. High-performance electrophoresis : Elimination of electroendosmosis and solute adsorption. Journal of Chromatography A. vol. 347, 1985, pp. 191-198.

International Search Report and Written Opinion dated May 11, 2017 for International PCT Patent Application No. PCT/US2016/064013.

Karger, et al. High-performance capillary electrophoresis in the biological sciences. J Chromatogr. Aug. 11, 1989;492:585-614.

Mack, et al. A systematic study in CIEF: defining and optimizing experimental parameters critical to method reproducibility and robustness. Electrophoresis. Dec. 2009;30(23):4049-58.

Manabe, et al. Separation of human plasma/serum proteins by capillary isoelectric focusing in the absence of denaturing agents. Electrophoresis. Jun. 1997;18(7):1159-65.

Michels, et al. Separation Methods and Orthogonal Techniques. State-of-the-Art and Emerging Technologies for Therapeutic Monoclonal Antibody Characterization vol. 2. Biopharmaceutical Characterization: The NISTmAb Case Study. Oct. 15, 2015. Chapter 5, pp. 237-284.

Mokaddem, et al. Online CIEF-ESI-MS in glycerol-water media with a view to hydrophobic protein applications. Electrophoresis. vol. 30, Issue 23, Dec. 2009. pp. 4040-4048.

Poitevin, et al. Comparison of different capillary isoelectric focusing methods—use of "narrow pH cuts" of carrier ampholytes as original tools to improve resolution. J Chromatogr A. Jul. 6, 2007;1155(2):230-6.

Righetti, et al. Carrier ampholytes for IEF, on their fortieth anniversary (1967-2007), brought to trial in court: the verdict. Electrophoresis. Nov. 2007;28(21):3799-810.

Roy, et al. Surface analysis, hydrophilic enhancement, ageing behavior and flow in plasma modified cyclic olefin copolymer (COC)-based microfluidic devices. Sensors and Actuators B: Chemical. vol. 150, Issue 2, Oct. 28, 2010, pp. 537-549.

Sung, et al. Chip-based microfluidic devices coupled with electrospray ionization-mass spectrometry. Electrophoresis. vol. 26, Issue 9, No. 9, May 2005. pp. 1783-1791.

Vagenende, et al. Mechanisms of protein stabilization and prevention of protein aggregation by glycerol. Biochemistry. Nov. 24, 2009;48(46):11084-96.

Wu, et al. Secrets of iCE Method Design for Protein Therapeutics. Protein Simple. Presentation Abstract. Tuesday Mar. 27, 2012. URL:<http://events.r20.constantcontact.com/register/event?llr=p9xbiodab&oeidk=a07e5nz3rtw6f41039b>.

Wu, J. J et al. Protein Analysis by Isoelectric Focusing in a Capillary Array With an Absorption Imaging Detector. Journal of Chromatography B, vol. 669, 1995, 5 pages.

(56) References Cited

OTHER PUBLICATIONS

Dai et al. Capillary Isoelectric Focusing-Mass Spectrometry Method for the Separation and Online Characterization of Intact Monoclonal Antibody Charge Variants. Anal Chem. Feb. 6, 2018;90(3):2246-2254.

Jin et al. Estimation of isoelectric points of human plasma proteins employing capillary isoelectric focusing and peptide isoelectric point markers. Electrophoresis. Sep. 2002;23(19):3385-91.

Minarik et al. Dispersion effects accompanying pressurized zone mobilisation in capillary isoelectric focusing of proteins. Journal of Chromatography A. Jun. 1996. 738(1):123-128.

Tang et al. Comparison of Protein Separations in Capillary Zone Electrophoresis and Capillary Isoelectric Focusing Interfacing with Electrospray Mass Spectrometry. Journal of Mass Spectrometry. Nov. 1996. 31(11):1284-1290.

\* cited by examiner

DEVICES AND METHODS FOR SAMPLE CHARACTERIZATION

CROSS REFERENCE TO RELATED APPLICATIONS

This application is continuation of U.S. patent application Ser. No. 15/363,908, filed Nov. 29, 2016, and entitled Devices and Methods for Sample Preparation, which is a non-provisional of and claims the benefit under 35 U.S.C. § 119(e) of U.S. Provisional Patent Application No. 62/260,944, filed Nov. 30, 2015, and U.S. Provisional Patent Application No. 62/338,074, filed May 18, 2016, each entitled "Devices, Methods, and Kits for Sample Characterization," the disclosure of each of which is hereby incorporated by reference in its entirety.

BACKGROUND

Some embodiments described herein relate to devices and methods for sample characterization and various uses thereof.

Separation of analyte components from a more complex analyte mixture on the basis of an inherent quality of the analytes, and providing sets of fractions that are enriched for states of that quality is a key part of analytical chemistry. Simplifying complex mixtures in this manner reduces the complexity of downstream analysis. It can be advantageous to perform two or more enrichment steps that are orthogonal, (e.g., based on different and/or unrelated qualities). In many cases, however, the process of performing orthogonal enrichment steps using known methods and/or devices is cumbersome, and can dilute the analyte beyond the sensitivity of the downstream analytical equipment. In addition, complications can arise when attempting to interface known enrichment methods and/or devices with analytical equipment and/or techniques.

Methods have been used to interface protein sample preparation techniques with downstream detection systems such as mass spectrometers. A common method is to prepare samples using liquid chromatography and collect fractions for mass spectrometry (LC-MS). This has the disadvantage of requiring protein samples to be digested into peptide fragments, leading to large number of sample fractions which must be analyzed and complex data reconstruction post-run. While certain forms of liquid chromatography can be coupled to a mass spectrometer, for example peptide map reversed-phase chromatography, these known techniques are restricted to using peptide fragments, rather than intact proteins, which limit their utility.

Another method to introduce samples into a mass spectrometer is electrospray ionization (ESI). In ESI, small droplets of sample and solution at a distal end of a capillary or microfluidic device are ionized to induce an attraction to the charged plate of a mass spectrometer. The droplet then stretches in this induced electric field to a cone shape ("Taylor cone"), which then releases small droplets into the mass spectrometer for analysis. Typically, this is done in a capillary, which provides a convenient volume and size for ESI. Capillaries however, provide a linear flow path that does not allow for multi-step processing.

Other work has been pursued with microfluidic devices. Microfluidic devices may be produced by various known techniques and provide fluidic channels of defined width that can make up a channel network designed to perform different fluid manipulations. These devices offer an additional level of control and complexity than capillaries. In connection with ESI, known devices include outwardly tapered tips and conductive edges in an attempt to enhance the ESI in these devices. The outward taper of known microfluidic devices used for ESI, however, exposes the fragile Taylor cone structure to potential disturbances by turbulent air flow and results in a contact surface geometry that will support only a limited range of cone radii, which limits control over the volume introduced to the mass spectrometer through ESI. Additionally, electrolysis of water at the conductive edge can lead to gas bubble formation, which interferes with the cone development.

One application for protein mass spectrometry is for characterization during the development and manufacturing of biologic and biosimilar pharmaceuticals. Biologics and biosimilars are a class of drugs which include, for example, recombinant proteins, antibodies, live virus vaccines, human plasma-derived proteins, cell-based medicines, naturally-sourced proteins, antibody-drug conjugates, protein-drug conjugates and other protein drugs.

Regulatory compliance demands that biologics require extensive testing during development and manufacture that is not required for small molecule drugs. This is because the manufacture of biologics has greater complexity due to, for example, using living material to produce the biologic, greater complexity of biologic molecule, greater complexity of the manufacturing process. Characteristics required to be defined include, for example, charge, efficacy, hydrophobic changes, mass, and glycosylation. Currently these tests are done independent of each other leading to a very time consuming and expensive process of characterizing biologics.

SUMMARY

Some embodiments described herein relate to devices and methods that can enable the analysis of analytes in an analyte mixture. For example, many specific characterizations of biologic proteins are required by regulatory agencies. Methods and devices described herein can be suitable for characterizing proteins and/or other analytes. In some embodiments, methods and devices described herein can relate to characterizing an analyte mixture that includes one or more enrichment steps performed to separate an analyte mixture into enriched analyte fractions.

In some instances, these analytes can be, for example, glycans, carbohydrates, DNA, RNA, intact proteins, digested proteins, antibody-drug conjugates, protein-drug conjugates, peptides, metabolites or other biologically relevant molecules. In some instances, these analytes can be small molecule drugs. In some instances, these analytes can be protein molecules in a protein mixture, such as a biologic protein pharmaceutical and/or a lysate collected from cells isolated from culture or in vivo.

Some embodiments described herein can include a first enrichment step, in which fractions containing a subset of the analyte molecules from the original analyte mixture are eluted one fraction at a time; these enriched analyte fractions are then subjected to another enrichment step. At the final enrichment step, the enriched analyte fractions are expelled for further analysis.

In some embodiments, one or more of the enrichment steps will be solid-phase separations. In some embodiments, one or more of the enrichment steps will be solution-phase separations.

In some embodiments, a final step concentrates the enriched analyte fractions before expulsion.

In some embodiments, substantially all of the enriched analyte fractions from the final enrichment step are expelled in a continuous stream. In some embodiments, a portion of the analyte mixture (e.g., a fraction of interest) will be expelled from a microfluidic device via an outlet configured to interface with an analytical instrument, such as a mass spectrometer or another device configured to fractionate and/or enrich at least a portion of the sample. Another portion of the analyte mixture (e.g., containing fractions other than the fraction of interest) can be expelled via a waste channel.

In some embodiments, the expulsion is performed using pressure, electric force, or ionization, or a combination of these.

In some embodiments, the expulsion is performed using electrospray ionization (ESI) into, for example, a mass spectrometer. In some embodiments a sheath liquid is used as an electrolyte for an electrophoretic separation. In some embodiments, a nebulizing gas is provided to reduce the analyte fraction to a fine spray. In some embodiments, other ionization methods are used, such as inductive coupled laser ionization, fast atom bombardment, soft laser desorption, atmospheric pressure chemical ionization, secondary ion mass spectrometry, spark ionization, thermal ionization, and the like.

In some embodiments, the enriched fractions will be deposited on a surface for further analysis by matrix-assisted laser desorption/ionization, surface enhanced laser desorption/ionization, immunoblot, and the like.

Some embodiments described herein relate to devices and methods for visualizing an analyte in an electrophoretic separation before and during the expulsion of enriched fractions.

Some embodiments described herein relate to devices and methods for visualizing an analyte during an enrichment step.

Some embodiments described herein relate to devices and methods for visualizing an analyte in a channel between enrichment zones.

In some embodiments, the visualization of an analyte can be performed via optical detection, such as ultraviolet light absorbance, visible light absorbance, fluorescence, Fourier transform infrared spectroscopy, Fourier transform near infrared spectroscopy, Raman spectroscopy, optical spectroscopy, and the like.

Some embodiments described herein relate to devices that can enable the analysis of analyte mixtures, in that they contain one or more enrichment zones and an orifice to expel enriched analyte fractions. In some embodiments, these devices include at least one layer which is not transmissive to light of a specific wavelength, and at least one layer which is transmissive to that specific wavelength. One or more portions of the layer which is not transmissive to light can define the one or more enrichment zones, such that the enrichment zones serve as optical slits.

In some embodiments, an analyte mixture can be loaded into a device through a tube or capillary connecting the device to an autosampler. In some embodiments, an analyte mixture can be loaded directly into a reservoir on the device.

In some embodiments, an orifice through which at least a portion of a sample can be expelled from a device is countersunk and/or shielded from air flow. In some embodiments, this orifice is not electrically conductive. As used herein, countersunk should be understood to mean that a portion of a substrate defines a recess containing the orifice, irrespective of the geometry of the sides or chamfers of the recess. Similarly stated, countersunk should be understood to include counterbores, conical and/or frustoconical countersinks, hemispherical bores, and the like.

Some embodiments described herein relate to an apparatus, such as a microfluidic device that includes a substrate constructed of an opaque material (e.g., soda lime glass, which is opaque to ultraviolet light). The substrate can define a microfluidic separation channel. Similarly stated, the microfluidic separation channel can be etched or otherwise formed within the substrate. The microfluidic separation channel can have a depth equal to the thickness of the substrate. Similarly stated, the microfluidic separation channel can be etched the full depth of the substrate (e.g., from the top all the way through to the bottom). In this way, the microfluidic separation channel can define an optical slit through the substrate. A transparent layer (e.g., a top layer) can be disposed on a top surface of the substrate, for example, sealing the top surface of the substrate. A transparent layer (e.g., a bottom layer) can also be disposed on a bottom surface of the substrate, such that both the top and the bottom of the microfluidic separation channel are sealed. In some embodiments, only a portion of the top layer and/or the bottom layer may be transparent. For example, the top layer and/or the bottom layer can define a transparent window in an otherwise opaque material; the window can provide optical access to, for example, the microfluidic separation channel.

Some embodiments described herein relate to an apparatus, such as a microfluidic device that includes a substrate. The substrate can define one or more enrichment zones or channels. For example, the substrate can define a first enrichment zone containing a media configured to bind to an analyte. Such a first enrichment zone can be suitable to separate an analyte mixture chromatographically. The apparatus can further include two electrodes electrically coupled to opposite end portions of a second enrichment zone. Such a second enrichment zone can be suitable to separate an analyte mixture electrophoretically. The second enrichment zone can intersect the first enrichment zone such that after a fraction of an analyte is separated, concentrated, and/or enriched in the first enrichment zone, it can be further separated, concentrated, and/or enriched in the second enrichment zone. The device can also include a recessed orifice. The orifice can be an outlet of the second enrichment channel and can be disposed on a countersunk or otherwise recessed surface of the substrate. The apparatus can be configured to expel a portion of an analyte mixture from the orifice via ESI. The recess can provide a stable environment for formation of a Taylor cone associated with ESI and/or can be configured to accept an inlet port of a mass spectrometer.

Some embodiments described herein relate to a method that includes introducing an analyte mixture into a microfluidic device that contains a separation channel. An electric field can be applied across the separation channel to effect a separation of the analyte mixture. The analyte mixture can be imaged during separation via a transparent portion of the microfluidic device. Similarly stated, a window and/or optical slit can provide optical access to the separation channel such that the whole separation channel or a portion thereof can be imaged while the separation is occurring. A fraction of the analyte mixture can be expelled from an orifice that is in fluid communication with the separation channel. For example, the fraction can be expelled via ESI. In some embodiments, the orifice can be disposed on a countersunk surface of the microfluidic device such that a Taylor cone forms within a recess defined by the countersunk surface.

Some embodiments described herein relate to a method that includes injecting an analyte into a microfluidic device containing a first separation channel and a second separation channel. The first separation channel can contain a medium configured to bind an analyte from the analyte mixture. Accordingly, when the analyte mixture is injected into the microfluidic device at least a fraction of the analyte mixture can be bound to the matrix and/or impeded from flowing through the first separation channel. For example, injecting the analyte into the microfluidic device can effect a chromatographic separation in the first separation channel. An eluent can be injected into the microfluidic device such that at least a fraction of the analyte is mobilized from the media. The first separation channel can be imaged while the analyte is mobilized. Imaging the first separation can include whole column (e.g., whole channel) imaging and/or imaging a portion of the channel. An electric field can be applied to the second separation channel when the imaging detects that the fraction is disposed at an intersection of the first separation channel and the second separation channel such that the fraction is mobilized into the second separation channel. For example, in some embodiments, the first separation channel can be orthogonal to the second separation channel. Similarly stated the first separation channel and the first separation channel can form a T-junction. The imaging can detect when a portion of the fraction (e.g., a portion of interest) is at the junction. Applying the electric field can mobilize the portion of the fraction (and, optionally, not other portions of the fraction that are not located at the junction) into the second separation channel for a second stage of separation. At least a portion of the fraction can be expelled from the microfluidic device.

DETAILED DESCRIPTION OF INVENTION

It is to be understood that both the foregoing general description and the following description are exemplary and explanatory only and are not restrictive of the methods and devices described herein. In this application, the use of the singular includes the plural unless specifically stated otherwise. Also, the use of "or" means "and/or" unless stated otherwise. Similarly, "comprise," "comprises," "comprising," "include," "includes" and "including" are not intended to be limiting.

Devices

Figure 1:
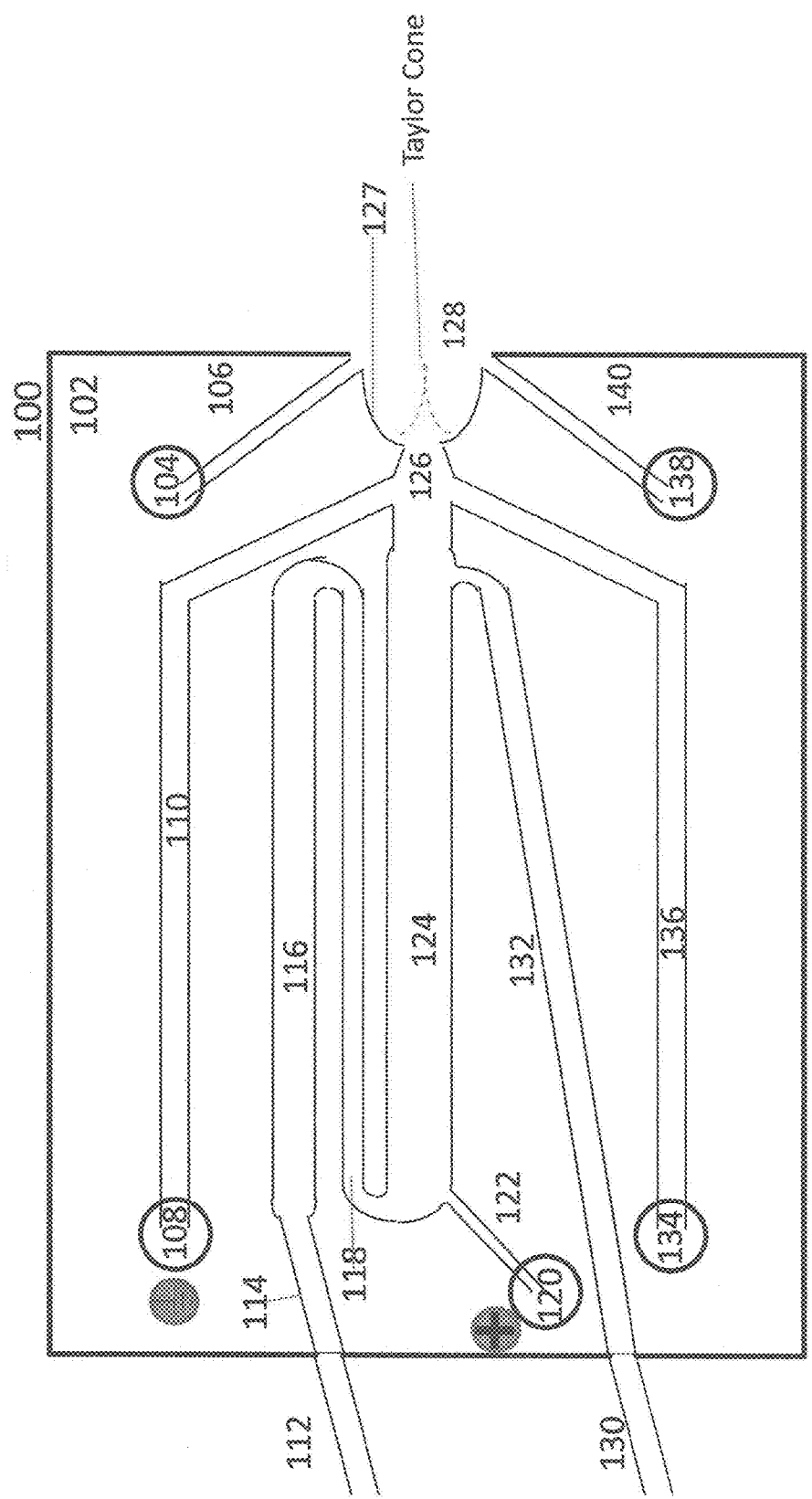
FIG. 1 is a schematic illustration of a device for two dimensional separation and ESI of an automatically loaded sample, according to an embodiment.

FIG. 1 is a schematic illustration of a device for two dimensional separation and ESI of an automatically loaded sample, according to an embodiment. A microfluidic network, 100, is defined by a substrate 102. The substrate is manufactured out of material which is compatible with the enrichment steps being performed. For example, chemical compatibility, pH stability, temperature, transparency at various wavelengths of light, mechanical strength, and the like are considered in connection with selection of material.

Substrate 102 may be manufactured out of glass, quartz, fused silica, plastic, polycarbonate, polytetrafluoroethylene (PTFE), polydimethylsiloxane (PDMS), silicon, polyfluorinated polyethylene, polymethacrylate, cyclic olefin copolymer, cyclic olefin polymer, polyether ether ketone and/or any other suitable material. Mixtures of materials can be utilized if different properties are desired in different layers of a planar substrate and/or any other suitable material. Mixtures of materials can be utilized if different properties are desired in different layers of a planar substrate.

Channels 106, 110, 114, 116, 118, 124 122, 126,132, 136 and 140 form the microfluidic network 100 and are fabricated into substrate 102. Similarly stated, the substrate 102 defines channels 106, 110, 114, 116, 118, 124 122, 126,132, 136 and/or 140.

Channels may be fabricated in the substrate through any channel fabrication method such as, for example, photolithographic etching, molding, machining, additive (3D) printing, and the like.

Analyte mixtures and external reagents can be loaded through tube/conduit 112, and excess reagent/waste can be removed through tube/conduit 130.

Tubes 112 and 130 can be manufactured out of any material compatible with the assay being performed, including, for example, fused silica, fused silica capillary tubes, silicone tubing, and/or PTFE tubing.

Channels 116 and 124 can be used to separate and/or enrich an analyte and/or a portion (e.g., a fraction) of an analyte. Channels 116 and/or 124 can be used to perform chromatographic separations (e.g., reversed-phase, immunoprecipitation, ion exchange, size exclusion, ligand affinity, dye affinity, hydrophobic interaction chromatography, hydrophilic interaction chromatography, pH gradient ion exchange, affinity, capillary electrokinetic chromatography, micellar electrokinetic chromatography, high performance liquid chromatography (HPLC), amino acid analysis-HPLC, ultra performance liquid chromatography, peptide mapping HPLC, field flow fractionation—multi angle light scattering) or electrophoretic separations (e.g., isoelectric focusing, capillary gel electrophoresis, capillary zone electrophoresis, isotachophoresis, capillary electrokinetic chromatography, micellar electrokinetic chromatography, flow counterbalanced capillary electrophoresis, electric field gradient focusing, dynamic field gradient focusing). For example, channel 116 can be derivatized or packed with material to perform a first enrichment step.

The material disposed into channel 116 and/or 124 can be selected to capture analytes based on, for example, hydrophobicity (reversed-phase), immunoaffinity (immunoprecipitation), affinity (efficacy), size (size exclusion chromatography), charge (ion exchange) or by other forms of liquid chromatography.

Many different methods can be used to dispose the enrichment material within channels 116 and/or 124. The walls can be directly derivatized with, for example, covalently bound or adsorbed molecules, or beads, glass particles, sol-gel or the like can be derivatized and loaded into these channels.

After sample is loaded into channel 116 wash solution and then elution reagent can be introduced through tube 112 and channel 114.

The elution process will depend on the enrichment method performed in channel 116. A suitable eluent can be selected to elute a fraction of the bound analyte. Some enrichment options may not require an elution step (e.g., size exclusion chromatography, electrophoretic separations, etc.).

The eluent or flow-through would then flow through channel 118 into channel 124. Channel 124 could be used to perform either a chromatographic or electrophoretic enrichment step.

Electrophoretic separations can be performed in channel 124 by using a power supply to apply an electric field between reservoir 108 and reservoir 120. Similarly stated, the device 100 can include electrodes in electrical contact with reservoir 108 and/or reservoir 120. The electrical ground of the power supply can be connected to the electrical ground of a mass spectrometer to provide continuity in the electric field from channel 124 to the mass spectrometer.

Any capillary electrophoresis (CE) electrophoretic method can be performed in channel 124—IEF, isotachophoresis (ITP), capillary gel electrophoresis (CGE), capillary zone electrophoresis (CZE), and the like. Alternately, non-electrophoretic enrichment methods can be performed in the channel 124.

In the case of IEF or ITP, concentrated purified sample bands would be mobilized, for example, by pressure or electrical means towards confluence 126. Sheath solution from reservoirs 108 and 134 could serve as sheath and catholyte.

The sheath/catholyte can be any basic solution compatible with the electrophoretic separation and mass spectrometry (MeOH/N$_4$OH/H$_2$O for example). Anolyte can be any acidic solution (e.g., phosphoric acid 10 mM).

Alternately, the electric field could be reversed and catholyte (NaOH) could be loaded in reservoir 120, and anolyte could be used as the sheath solution in reservoirs 108 and 134.

The confluence 126 is where the enriched analyte fraction mixes with the sheath solution. As the analyte fractions in channel 124 are mobilized, solution will be pushed through confluence 126 out to orifice 128.

The orifice 128 can be disposed within a recess defined by surface 127 of substrate 102. For example, surface 127 can be a countersunk ESI surface. For example, as shown in FIG. 1, the enriched analyte solution, being electrically grounded through well 108, can form a Taylor cone emanating from orifice 128, which is disposed entirely within a recess defined by surface 127. The orifice 128 and/or surface 127 can be oriented toward a mass spectrometer inlet, which can have a voltage potential difference relative to well 108. As spray breaks off from the cone structure toward the mass spectrometer, it can be flanked by nebulizing gas provided through channels 106 and 140 before it leaves the substrate 102. The nebulizing gas can be any inert or non-reactive gas (e.g., Argon, Nitrogen, and the like).

Additionally, using a sheath liquid and/or nebulizing gas can allow for the use of an ion depleting step as the last "on-device" step. The sheath liquid allows for replenishment of ion potential lost during an IEF charge assay concentrating step prior to ESI, and nebulization provides the sample in a fine mist for the off line analysis.

By generating the Taylor cone on surface 127, the cone is created in a stable pocket or recess and is protected from disturbing air currents. Additionally, the conical geometry surrounding the countersunk orifice has a naturally expanding contact surface that will accommodate a wider range of Taylor cone radial cross sections, allowing for a wider range of flow rates into the mass spectrometer.

Orifice 128 can be positioned in proximity to an inlet port of a mass spectrometer. In some instances, the surface 127 can be configured such that an inlet port of a mass spectrometer can be disposed within a recess defined by the surface 127.

Figure 2:
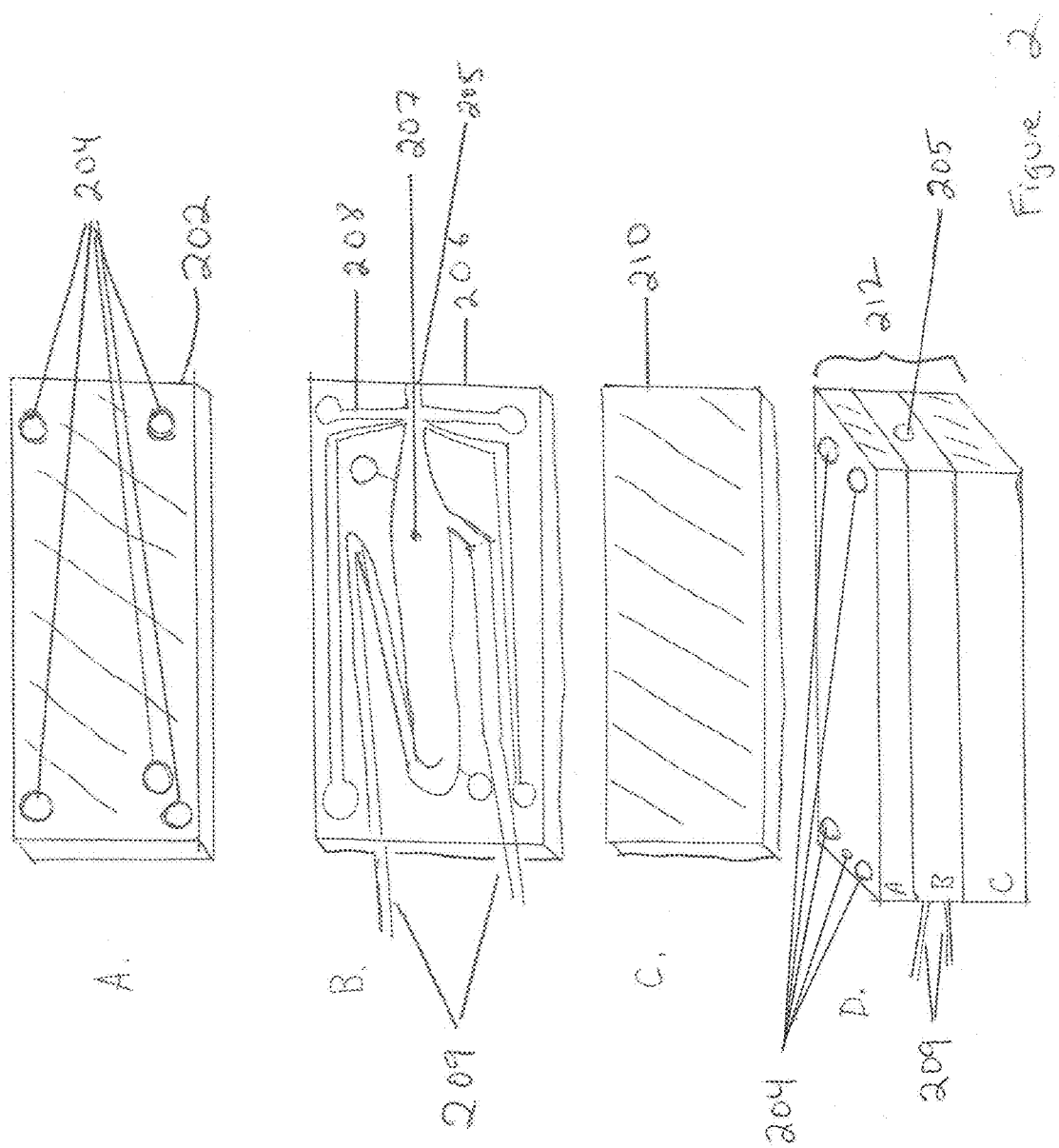
FIG. 2 is a schematic exploded view of a device having three layers, according to an embodiment.

FIG. 2 a schematic exploded view of a device 212 having three layers, according to an embodiment. FIG. 2A shows a top layer 202 of device 212, according to an embodiment. FIG. 2B shows a middle layer 206 of device 212, according to an embodiment. FIG. 2C shows a bottom layer 210 of device 212, according to an embodiment. FIG. 2D shows the device 212 as assembled, according to an embodiment. Each of the three layers 202, 206, 210 may be made of any material compatible with the assays the device 212 is intended to perform.

In some embodiments, layer 202 will be fabricated from a material which is transparent to a specific wavelength, or wavelength range, of light. As used herein, "transparent" should be understood to mean that the material has sufficient transmittance to allow the amount of light having a specific wavelength or range of wavelengths on one side of the material to be quantified by a detector on the other side. In some instances, material with a transmissivity of 30%, 50%, 80%, 95%, or 100% is transparent. In some embodiments, a wavelength range of interest will include the middle ultraviolet range (e.g., 200 nm-300 nm), and materials such as, for example, glass, quartz, fused silica and UV-transparent plastics such as polycarbonates, polyfluorinated polyethylene, polymethacrylate, cyclic olefin polymer, cyclic olefin copolymer, and other UV-transparent materials can be used as transparent materials. In some embodiments, the light spectrum of interest will be expanded beyond the visible spectrum (e.g., 200-900 nm).

Through-holes, 204, are fabricated in layer 202 to allow pressure and electrical interface to a channel network in a lower layer (e.g., layer 208) from outside the device.

FIG. 2B shows the internal middle layer 206 of device 212 containing the channel network 208. The channel network is designed to interface with the through-holes fabricated in the top layer 202. The channel network 208 contains inlet and outlet tubes/conduits 209, and orifice 205 for expelling enriched analyte fractions, and a viewable enrichment zone 207. Enrichment zone 207 is fabricated so its depth is the full thickness of the layer 206. In other embodiments, zone 207 can be less than the full thickness of layer 206.

In some embodiments, layer 206 will be fabricated from a material which is opaque and/or not transparent to a specific wavelength, or wavelength range, of light. As used herein, "opaque" should be understood to mean the material has insufficient transmittance to allow the amount of light on one side of the material to be quantified by a detector on the other side, and will effectively block this light except in the regions where the zone in the channel network is as deep as the full thickness of layer 206.

FIG. 2C shows a bottom layer 210 of device 212. Bottom layer 210 can be, for example, a solid substrate. In some embodiments, bottom layer 210 can be fabricated from a material with the same transmittance as layer 202.

FIG. 2D shows the device 212 including top layer 202, the middle layer 206, and the bottom layer 210, as assembled, according to an embodiment. Inlet and outlet tubes 209, reservoirs 204 and orifice 205 can still be accessed after the device 210 is assembled. In some embodiments, the entire top layer 202 and/or the entire bottom layer 210 can be transparent. In other embodiments, a portion of the top layer 202 and/or a portion of the bottom layer 210 can be opaque with another portion of the top layer 202 and/or the bottom layer 210 being transparent. For example, the top layer 210 and/or the bottom layer 210 can define an optical window that aligns with at least a portion of the enrichment zone 207 when the device 212 is assembled.

Figure 3:
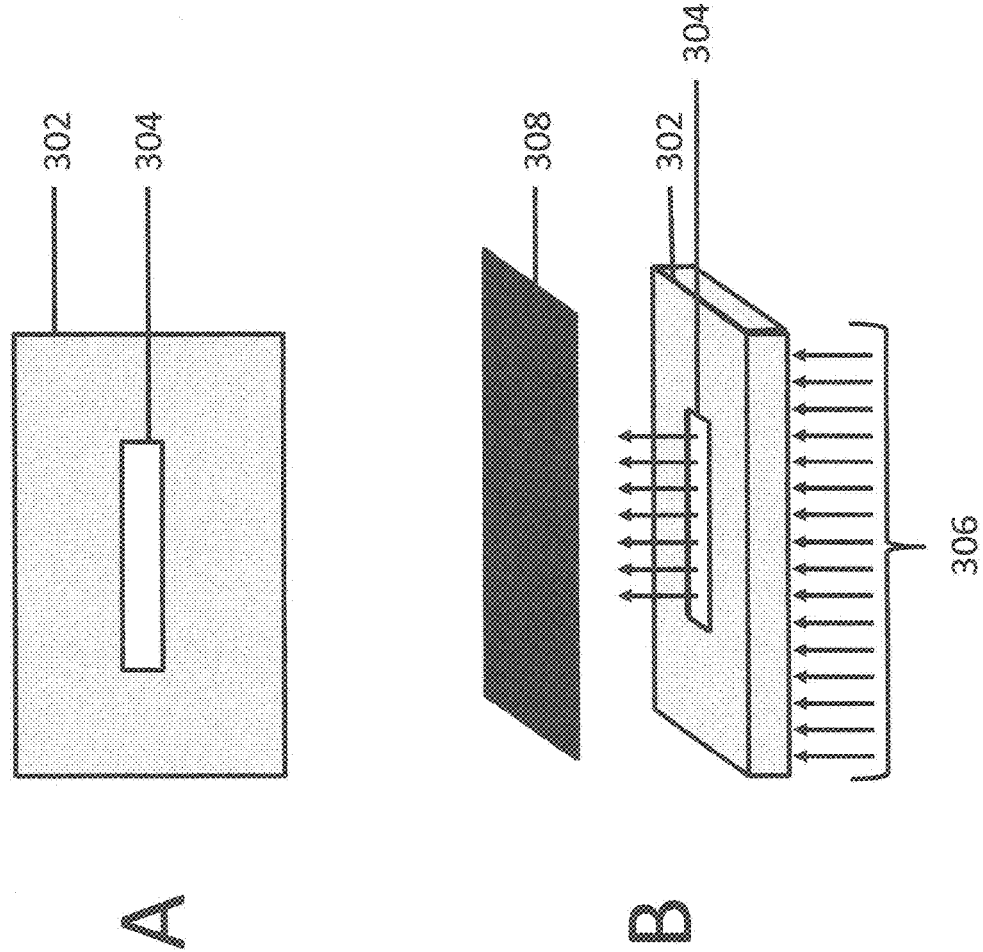
FIG. 3 is a schematic of a light path through a microfluidic device, according to an embodiment.

FIG. 3 is a schematic of a light path through a microfluidic device 302, according to an embodiment. FIG. 3A shows a top view of the microfluidic device 302. FIG. 3B shows the microfluidic device 302 positioned between a light source 306 and a detector 308. The detector 308 is positioned to measure light passing through the device 302. While not illustrated in FIG. 3, the microfluidic device 302 can have a similar channel structure as described in FIGS. 1 and 2, but the channel structure is not shown for ease of reference. In some embodiments, a portion of top surface of the microfluidic device 302 is opaque and completely or substantially obscures light projected from the light source 306 from reaching the detector 308. The portion of the opaque top surface substantially prevents the transmission of light through the device at those portions where detection of sample properties is not desired. For example, the microfluidic device 302 in some embodiments is not opaque (e.g., allows some light to pass through) over one or more channel region(s) 304, as the channel 304 transverses the entire thickness of a non-transparent layer.

In some embodiments, this transparent channel region(s) 304, can be an enrichment zone, where optical detection can be used to detect analyte, monitor the progress of the enrichment and/or monitor enriched analyte fraction(s) as they are expelled from the device. In some embodiments, changes in the amount of light passing through transparent channel 304 will be used to measure the absorbance of the analyte fractions while they are in this channel. Thus, in some embodiments, channel region(s) 304 define an optical slit, such that the light source 306 positioned on one side of the microfluidic device 302 effectively illuminates the detector 308 only through the transparent channel region(s) 304. In this way, stray light (e.g., light that does not pass thorough the transparent channel regions(s) and/or a sample) can be effectively blocked from the detector 308, which can reduce noise and improve the ability of the detector 308 to observe sample within the transparent channel region(s) 304. In some embodiments, the transparent channel regions(s) 304 will be between two enrichment zones, and can be used to detect analyte fractions as they are eluted from the upstream enrichment zone.

Methods

Figure 6:
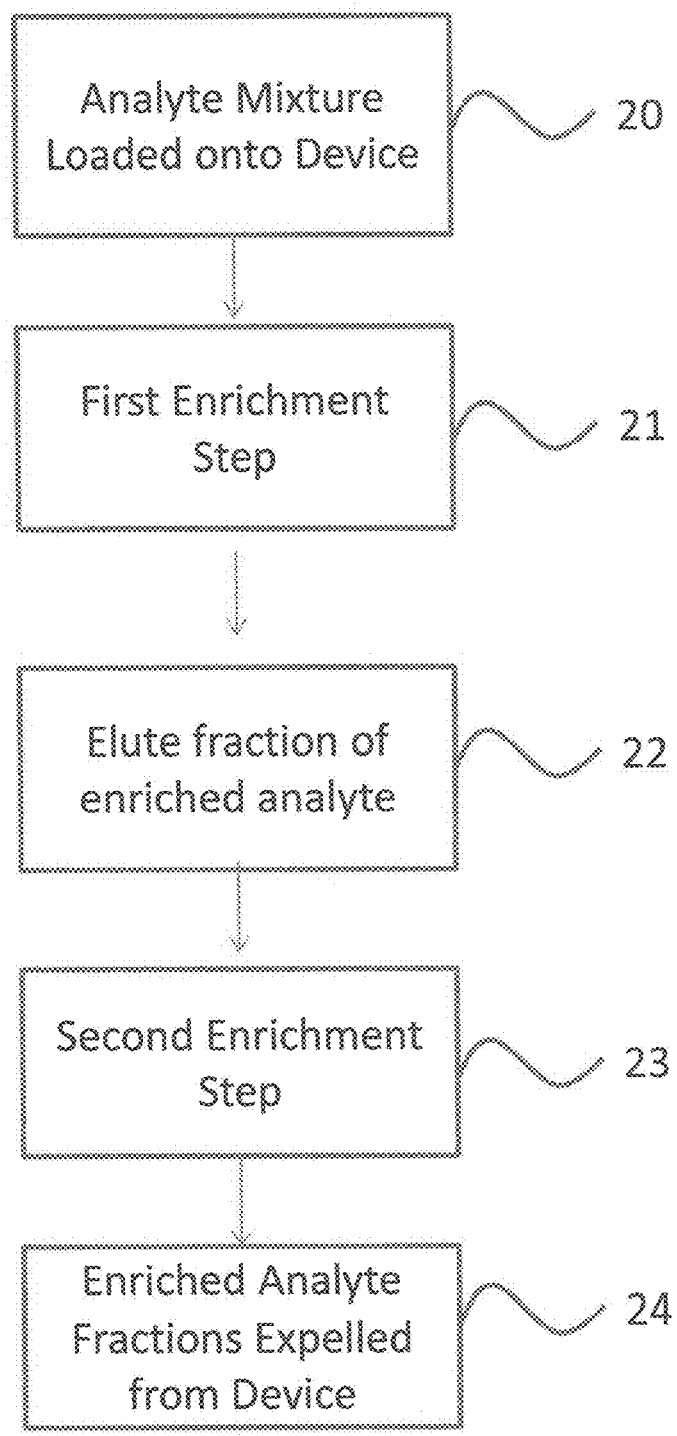
FIG. 6 is a flowchart of an exemplary method for analyte characterization.

FIG. 6 illustrates a method of analyte mixture enrichment according to an embodiment. The method includes loading and/or introducing an analyte mixture onto a microfluidic device, at 20. The microfluidic device can be similar to the microfluidic devices described above with reference to FIGS. 1-3. In some embodiments, the analyte mixture can be, for example, glycans, carbohydrates, DNA, RNA, intact proteins, digested proteins, peptides, metabolites, vaccines, viruses and small molecules. In some embodiments, the analyte mixture can be a mixture of proteins, such as a lysate of cultured cells, cell-based therapeutics, or tumor or other tissue derived cells, recombinant proteins, including biologic pharmaceuticals, blood derived cells, perfusion or a protein mixture from any other source. The analyte mixture may be loaded directly onto the device, or may be loaded onto an autosampler for serial analysis of multiple mixtures.

The microfluidic device can include a first separation channel and/or enrichment zone. In some embodiments, the first separation channel and/or enrichment zone can be configured for chromatographic separation. For example, the first separation channel and/or enrichment zone can contain a media configured to bind an analyte from the analyte mixture and/or otherwise effect a chromatographic separation. At 21, a first enrichment can be performed; for example, a chromatographic separation can be performed in the first separation channel and/or enrichment zone. In some embodiments, such as embodiments in which the analyte mixture is a protein mixture, the first enrichment, at 21, can simplify the protein mixture. The first enrichment, at 21, can be based on any discernable quality of the analyte.

This enriched analyte fraction is then eluted, at 22. For example, an eluent can be injected into the microfluidic device to mobilize the enriched analyte fraction from media disposed within the first separation channel and/or enrichment zone. In some embodiments, the enrichment and/or mobilization of the enriched analyte fraction can be imaged. For example, as discussed above, the first separation channel and/or enrichment zone can define an optical slit. Light can be projected onto the microfluidic device and a detector can detect light passing through the first separation channel and/or enrichment zone. The sample, or a portion thereof can be detected via absorbance and/or fluorescence imaging techniques.

The microfluidic device can include a second separation channel and/or enrichment zone. In some embodiments, the second separation channel and/or enrichment zone can be configured for electrophoretic separation. At 23, a second enrichment can be performed, for example, on the eluate. For example, an electric field and/or electric potential can be applied across the second separation channel and/or enrichment zone.

In some embodiments, the second enrichment can be initiated, at 23, when a fraction of the analyte mixture is disposed at an intersection of the first separation channel and/or enrichment zone and the second separation channel and/or enrichment zone. For example, the first separation channel and/or enrichment zone can be monitored (e.g., imaged) and an electric potential, and/or electric field can be applied when a fraction of interest reaches the intersection.

In some embodiments, the second enrichment, at 23, can provide fractions enriched based on charge characteristics (charge isoforms). Such enrichments can include, for example, gel isoelectric focusing, isoelectric focusing with mobilization, isoelectric focusing with whole column imaging, ion exchange chromatography, pH gradient exchange chromatography, isotachophoresis, capillary zone electrophoresis, capillary gel electrophoresis or other enrichment techniques that are, for example, charge-based.

Although the first enrichment, at 21, has been described as a chromatographic enrichment and the second enrichment, at 23, has been described as electrophoretic, it should be understood the any suitable enrichment can be performed in any suitable sequence. For example, the first enrichment, at 21, and the second enrichment, at 23, can both be chromatographic or both be electrophoretic. As another example, the first enrichment, at 21, can be electrophoretic, and the second enrichment, at 23, can be chromatographic.

In some embodiments, one or more enrichments can provide fractions enriched based on hydrophobic changes, such as oxidation. Such enrichments can include, for example, reversed-phase chromatography, hydrophobic interaction chromatography, hydrophilic interaction chromatography, or other enrichment techniques that are, for example, hydrophobicity-based.

In some embodiments, one or more enrichments can provide fractions enriched based on post-translational modifications, glycoforms including galactosylation, fucosylation, sialylation, mannose derivatives and other glycosylations, as well as glycation, oxidation, reduction, phosphorylation, sulphanation, disulfide bond formation, deamidiation, acylation, pegylation, cleavage, antibody-drug conjugation (ADC), protein-drug conjugation, C-terminal lysine processing, other naturally and non-naturally occurring post-translational modifications and other chemical and structural modifications introduced after translation of the protein, and the like. Such enrichments can include, for example, binding assays and the like.

In some embodiments, one or more enrichments can provide fractions enriched based on hydrophobic changes, such as oxidation. Such enrichments can include, for example, reversed-phase chromatography, hydrophobic interaction chromatography, hydrophilic interaction chromatography, or other enrichment techniques that are hydrophobicity-based.

In some embodiments, one or more enrichments can provide fractions enriched based on primary amino acid sequence, such as caused by mutation, amino acid substitution during manufacture and the like. Such enrichments can include, for example, separating by charge isoforms, hydrophobic changes, or other enrichment techniques that can distinguish between primary amino acid sequence differences.

In some embodiments, one or more enrichments can provide fractions enriched based on efficacy. Such enrichments can include, for example, bioassays, enzyme inhibition assays, enzyme activation assays, competition assays, fluorescence polarization assays, scintillation proximity assays, or other enrichment techniques that are efficacy-based and the like.

In some embodiments, one or more enrichments can provide fractions enriched based on affinity. Such enrichments can include, for example, solution phase binding to target, binding to bead based targets, surface bound target, immunoprecipitation, protein A binding, protein G binding and the like.

In some embodiments, one or more enrichments can provide fractions enriched based on mass or size. Such enrichments can include, for example, poly acrylamide gel electrophoresis, capillary gel electrophoresis, size exclusion chromatography, gel permeation chromatography, or other enrichment techniques that are mass-based.

In some embodiments, the analyte mixture will go through more than two enrichments and/or enrichment channels before being expelled from the device.

At 24, an enriched analyte fraction can be expelled from the device. In some embodiments, the enriched analyte fraction can be expelled via IEF. Expelling the enriched analyte fraction, at 24, can concentrate the analyte fractions before they are expelled from.

In some embodiments the analyte fractions are expelled, at 24, using an ionization technique, such as electrospray ionization, atmospheric pressure chemical ionization, and the like.

In some embodiments, the analyte fractions are expelled, at 24, using electrokinetic or hydrodynamic forces.

In some embodiments, the enriched protein fractions are expelled, at 24, from the device in a manner coupled to a mass spectrometer.

Mass of an analyte expelled from the microfluidic device (e.g., a biologic or biosimilar) can be measured, for example, through time-of-flight mass spectrometry, quadrupole mass spectrometry, Ion trap or orbitrap mass spectrometry, distance-of-flight mass spectrometry, Fourier transform ion cyclotron resonance, resonance mass measurement, and nanomechanical mass spectrometry.

In some embodiments pI markers are used to map pI ranges in the visualized IEF channel (e.g., the first separation channel and/or enrichment zone and/or the second separation channel and/or enrichment zone). In some embodiments, pI markers or ampholytes can be used to determine the pI of the analyte by their presence in downstream mass spectrometry data.

In some embodiments, IEF can be monitored during the mobilization and ESI. In this way, mass spectrometry data can be correlated to peaks in the IEF, which can maintain and/or improve peak resolution.

Figure 7:
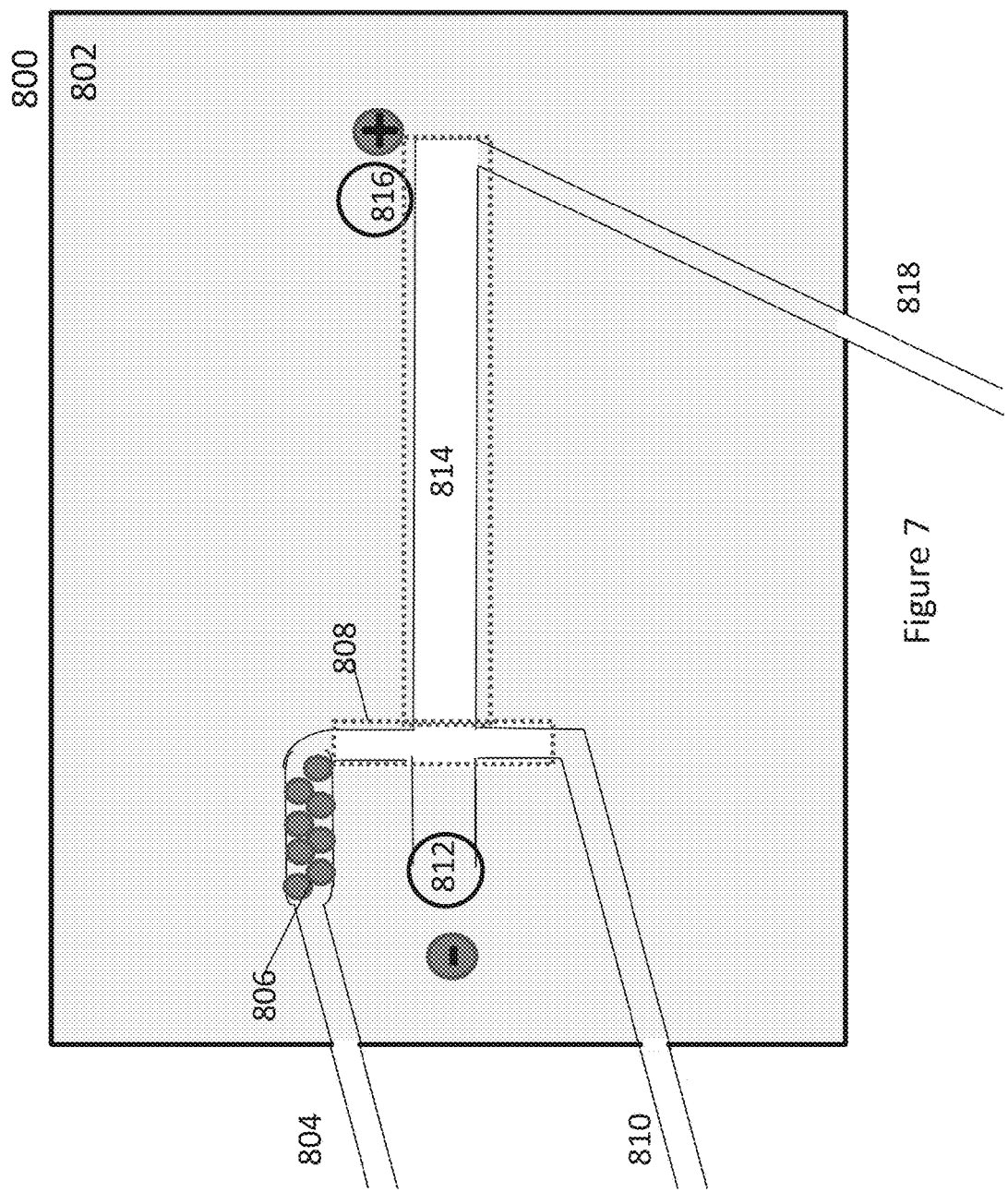
FIG. 7 is a schematic of a microfluidic device, according to an embodiment.

In some embodiments, the analyte mixture and/or a portion thereof can be mobilized within the microfluidic device using pressure source. In some embodiments, mobilization is done with hydrostatic pressure. In some embodiments, mobilization is chemical immobilization. In some embodiments, mobilization is electrokinetic mobilization FIG. 7 is a schematic of a microfluidic device, according to an embodiment. A microfluidic network, 800, is disposed in and/or defined by a substrate, 802. The substrate is manufactured out of material which is compatible with the enrichment steps being performed. For example, chemical compatibility, pH stability, temperature, transparency at various wavelengths of light, mechanical strength, and the like may be of concern when selecting the material Substrate 802 may be manufactured out of glass, quartz, fused silica, plastic, polycarbonate, PTFE, PDMS, silicon, polyfluorinated polyethylene, polymethacrylate, cyclic olefin copolymer, cyclic olefin polymer, polyether ether ketone and/or any other suitable material. Mixtures of materials can be utilized if different properties are desired in different layers of a planar substrate.

Channels 806, 808, 810, 811, 817, 814, 812 form a channel network and are fabricated into (e.g., defined by) substrate 802.

Channels may be fabricated in the substrate through any channel fabrication method such as photolithographic etching, molding, machining, additive (3D) printing, and the like.

Analyte mixtures and external reagents can be loaded through tube 804, and excess reagent/waste can be removed through tube 810 and 818.

Tubes 804 810, and/or 818 can be manufactured out of any material compatible with the assay being performed, including fused silica, fused silica capillary tubes, silicone tubing, PTFE tubing, and the like.

Channels 806 and 814 can be designated as separation/enrichment zones. Either of channel 806 and/or 814 can be used to perform chromatographic separations (reversed phase, immunoprecipitation, ion exchange, size exclusion, ligand affinity, dye affinity, hydrophobic interaction, affinity, capillary electrokinetic chromatography, micellar electrokinetic chromatography and/or the like) or electrophoretic separations (isoelectric focusing, capillary gel electrophoresis, capillary zone electrophoresis, isotachophoresis, capillary electrokinetic chromatography, micellar electrokinetic chromatography, flow counterbalanced capillary electrophoresis, electric field gradient focusing, dynamic field gradient focusing, and/or the like). For example, channel 806 can be derivatized or packed with material to perform a first enrichment step, represented by darker circles in channel 806.

The material disposed into channel 806 can be selected to capture analytes based on hydrophobicity (reversed phase), affinity (efficacy), size (size exclusion chromatography), charge (ion exchange), immunoaffinity (immunoprecipitation), protein-protein interaction, DNA-protein interaction, aptamer-base capture, small molecule-base capture or by other forms of liquid chromatography and the like.

Many different methods can be used to dispose the enrichment material within channel 806 and/or 814. The walls can be directly derivatized with covalently bound or adsorbed molecules, or beads, glass particles, sol-gel or the like can be derivatized and loaded into these channels, or channels can be packed with a sieving material such as— linear polymer solutions such as linear polyacrylamide (LPA), polyvinylpyrrolidone (PVP), polyethylene oxide (PEO), dextran, and the like, cross-linked polymer solutions such as polyacrylamide and the like, matrices for liquid chromatography, or other materials.

Chemically reactive solutions may be added depending on the particular assay performed. In some cases, derivatization of material may occur after it is loaded into channel 806 (or channel 814), by adding molecules which will adsorb or covalently bond to the loaded material, or can chemically cross link reactive elements to the material. For example, material coated with an antibody-binding molecule such as protein A, protein G, epoxy or the like, could be disposed into channel 806. Subsequent rinsing with an antibody solution would leave the material coated with antibody and able to participate in immunoaffinity capture. In some cases, the antibody may be mixed with a target analyte or lysate so that the antibody can bind its target in free solution before being coated onto the material.

After enrichment materials are loaded onto device, sample is loaded via tube 804 into channel 806. Subsequently, wash solutions and elution reagents can be introduced through tube 804 to channel 806.

In some cases, detection reagents will be added to bind to captured material. Numerous labeling reagents are available that can covalently attach detection moieties such as fluorophores, chromophores or other detection molecules to the target proteins at terminal ends of the polypeptide, and by attachment to amino acid side chains such as lysine, cysteine and other amino acid moieties. Covalently bound detection moieties allow for the protein to be detected through fluorescence excitation, chromophoric assay, or other indirect means. In some cases, the target protein can remain unlabeled and detected through native absorbance at 220 nm, 280 nm or any other wavelength at which the protein will absorb light, or native fluorescence. In some cases, the protein will be detected using non-covalently bound fluorogenic, chromogenic, fluorescent or chromophoric labels, such as SYPRO® ruby, Coomassie blue and the like.

In some cases, detection reagents will be added directly to channel 814 to aid detection.

The elution process will depend on the enrichment method performed in channel 806. It will be selected to elute at least a fraction of the bound analyte. In some cases, this can be accomplished with a combination of heat and sodium dodecyl sulfate (SDS), or other detergents, glycine, urea, or any other method which will induce the release of the captured analyte. Some enrichment options may not require a direct elution step (e.g. size exclusion chromatography). In some cases, elution will be followed by denaturation.

The eluent would then flow through channel 808 into the next separation/enrichment zone, channel 814. Channel 814 could be used to perform either a chromatographic or electrophoretic enrichment step.

Electrophoretic separations can be performed in channel 814 by using a power supply to apply an electric field between reservoir 812 and reservoir 816. When eluate from channel 806 passes through the intersection of channels 808 and 814, the electric field can be enabled, loading analyte into channel 814. In some case, the analyte will be negatively charged, such as in the standard gel electrophoresis mode where protein analyte is saturated with a negatively charged detergent like SDS. However, the polarity of channel 814 can easily be reversed to accommodate systems where for example, a protein analyte is saturated with a positively charged detergent such as cetyl trimethylammonium bromide (CTAB) or the like. In other cases, a protein analyte may be coated with a neutral detergent, or no detergent—such as in native gel electrophoresis. In this case, polarity will be selected based on the anticipated charge of the protein target in the buffer system selected, so that the protein analyte will migrate into channel 814.

Any CE electrophoretic method can be performed in channel 814—IEF, ITP, CGE, CZE, and the like. Alternately, non-electrophoretic enrichment methods can be performed in the channel.

Analyte in channel 814 can be viewed by whole column imaging, partial column imaging, and/or by single point detection.

In some cases, the enrichment material in channels 806, 814 or both may be removed and replenished with fresh material so that the device can be used on another analyte sample.

In some cases, a channel design such as FIG. 7 may be repeated multiple times on a device, so that more than one analyte sample may be analyzed in parallel.

EXAMPLES

Aspects of embodiments may be further understood in light of the following examples, which should not be construed as limiting in any way.

Example 1—Characterize Protein Charge on Chip Before Mass Spectrometry (MS)

Figure 4:
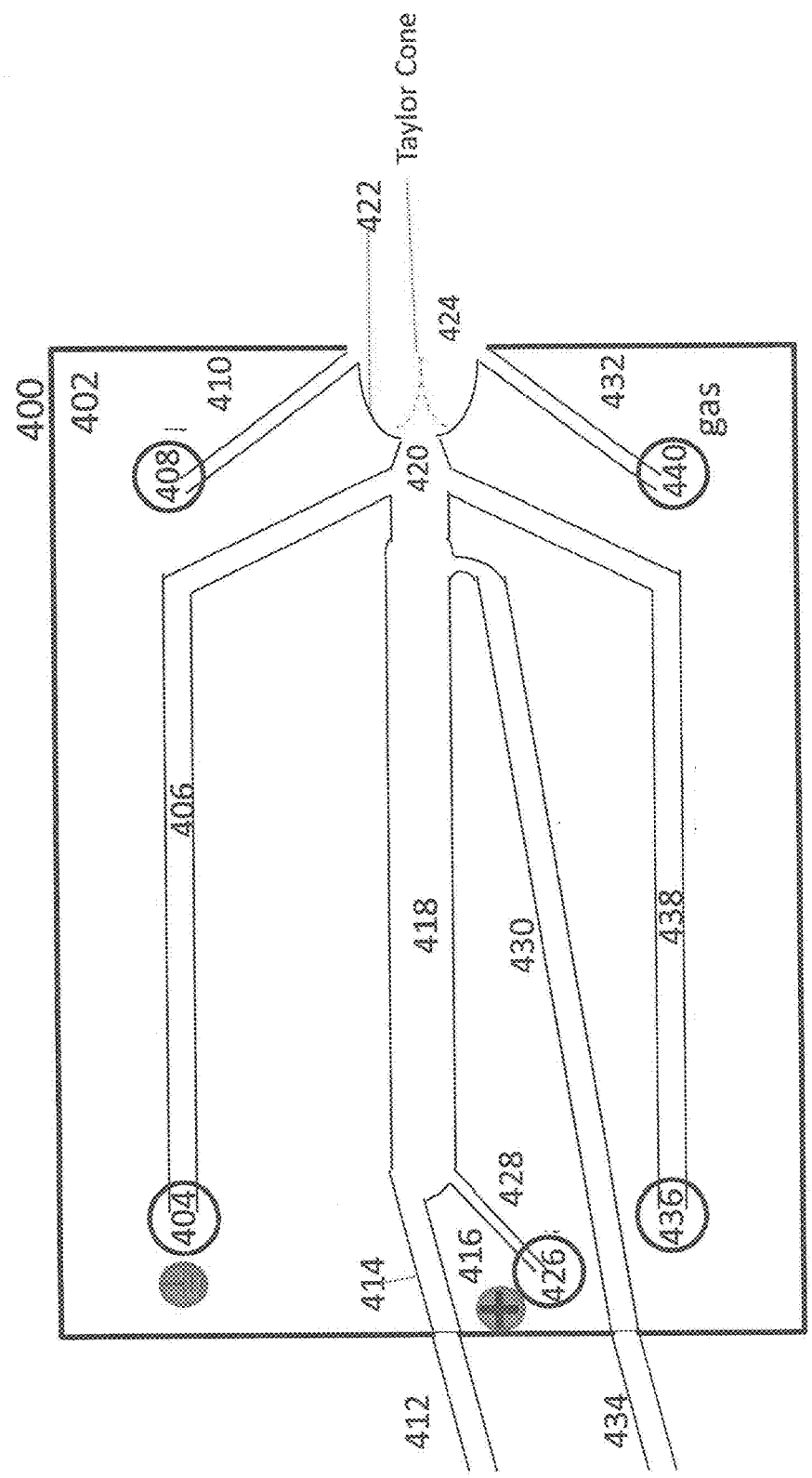
FIG. 4 is a schematic illustration of a device for isoelectric focusing (IEF) and ESI of an automatically loaded sample, according to an embodiment.

For this example, the channel network shown in FIG. 4 is fabricated from a plate of soda lime glass, which has very low transmission of 280 nm light using a standard photolithographic etching technique. The depth of the enrichment channel 418 is the same as the thickness of the glass layer 402, i.e., the enrichment channel 418 passes all the way from the top to bottom of this glass plate 402. The device 400 can be illuminated by a light source disposed on one side of device 400 and imaged by a detector on disposed on an opposite side of device 400. Because substrate 402 is opaque, but enrichment channel 418 defines an optical slit, the substrate 402 can block light that does not pass through the enrichment channel 418, blocking stray light and improving resolution of the imaging process.

The glass layer 402 is sandwiched between two fused silica plates, which are transmissive (e.g., transparent) to 280 nm light. As in FIG. 2, the top plate contains through holes for the instrument and user to interface with the channel network, while the bottom plate is solid. The 3 plates are bonded together at 520° C. for 30 minutes. The inlet and outlet tubing is manufactured from cleaved capillary (100 µm ID, polymicro), bonded to the channel network.

The device is mounted on an instrument containing a nitrogen gas source, heater, positive pressure pump (e.g., Parker, T5-1IC-03-1EEP), electrophoresis power supply (Gamm High Voltage, MC30) terminating in two platinum-iridium electrodes (e.g., Sigma-Aldrich, 357383), UV light source (e.g., LED, qphotonics, UVTOP280), CCD camera (e.g., ThorLabs, 340UV-GE) and an autosampler for loading samples onto the device. The power supply shares a common earth ground with the mass spectrometer. The instrument is controlled through software (e.g., labView).

Protein samples are pre-mixed with ampholyte pH gradient and pI markers before placing into vials and loading onto the autosampler. They are serially loaded from an autosampler via the inlet 412 onto the microfluidic device 400 through the enrichment channel 418 and out of the device to waste 430 through the outlet 434.

The sheath/catholyte fluid (50% MeOH, $N_4OH/H_2O$) is loaded onto the two catholyte wells 404, 436, anolyte (10 mM $H_3PO_4$) onto the anolyte well 426, and the source of heated nitrogen gas is attached to the two gas wells 408, 440.

After all reagents are loaded, an electric field of +600V/cm is applied from anolyte well 426 to catholyte wells 404, 436 by connecting the electrodes to the anolyte well 426 and catholyte wells 404, 436 to initiate isoelectric focusing. The UV light source is aligned under the enrichment channel 418, and the camera is placed above the enrichment channel 418 to measure the light that passes through the enrichment channel 418, thereby detecting the focusing proteins by means of their absorbance. The glass plate 402, being constructed of soda-lime glass, acts to block any stray light from the camera, so light not passing through the enrichment channel 418 is inhibited from reaching the camera, increasing sensitivity of the measurement.

Images of the focusing proteins can be captured continuously and/or periodically during IEF. When focusing is complete, low pressure will be applied from the inlet 412, mobilizing the pH gradient toward the orifice 424. The electric field can be maintained at this time to maintain the high resolution IEF separation. Continuing to image the enrichment channel 418 during the ESI process can be used to determine the pI of each protein as it is expelled from the orifice 424.

As the enriched protein fraction moves from the enrichment channel 418 into the confluence 420, it will mix with the sheath fluid, which can flow from the catholyte wells 404, 436 to the confluence 420 via sheath/catholyte fluid channels 406, 438. Mixing enriched protein fractions with the sheath fluid can put the protein fraction in a mass spectrometry compatible solution, and restore charge to the focused protein (IEF drives proteins to an uncharged state), improving the ionization.

The enriched protein fraction then continues on to the orifice 424, which can be defined by a countersunk surface 422 of the glass plate 402. The enriched protein fraction can create a Taylor cone once caught in the electric field between the sheath fluid well ground and mass spectrometer negative pole.

As solution continues to push at the Taylor cone from the enrichment channel 418, small droplets of fluid will be expelled from the Taylor cone and fly towards the mass spectrometer inlet. Nitrogen gas (e.g., at 150° C.) can flow from the gas wells 408, 440, down gas channels 410, 432 and form nitrogen gas jets which flank the Taylor cone which can convert droplets emanating from the Taylor cone to a fine mist before leaving the microfluidic device, which can aid detection in the mass spectrometer. Adjusting pressure from the inlet 412 can adapt Taylor cone size as needed to improve detection in mass spectrometer.

Example 2—Reversed-Phase→IEF→MS

Example 2 can be similar to example 1, but is described with reference to FIG. 1. The channel 116 can be a first enrichment zone loaded with sol-gel derivatized with C18. After loading protein, a volume of eluent ($MeCN/H_2O$ with IEF ampholytes and standards) can be loaded into channel 116 to elute the least hydrophobic proteins trapped on the sol gel. The eluate is directed to channel 124, which can be a second enrichment zone where IEF, UV absorbance monitoring and finally ESI take place as described in example 1. Once the ESI of the first eluate is complete, a volume of higher MeCN concentration is used to elute the next lowest hydrophobic protein fraction.

Example 3—Efficacy→IEF→MS

Example 3 can be similar to example 2, but biologic drug target derivatized beads can be loaded into channel 116 and used to capture protein. Affinity of reaction is characterized through elution by solution phase target (competitive), salt, pH, or the like.

Example 4—Reversed-Phase→Capillary Zone Electrophoresis→MS

Figure 5:
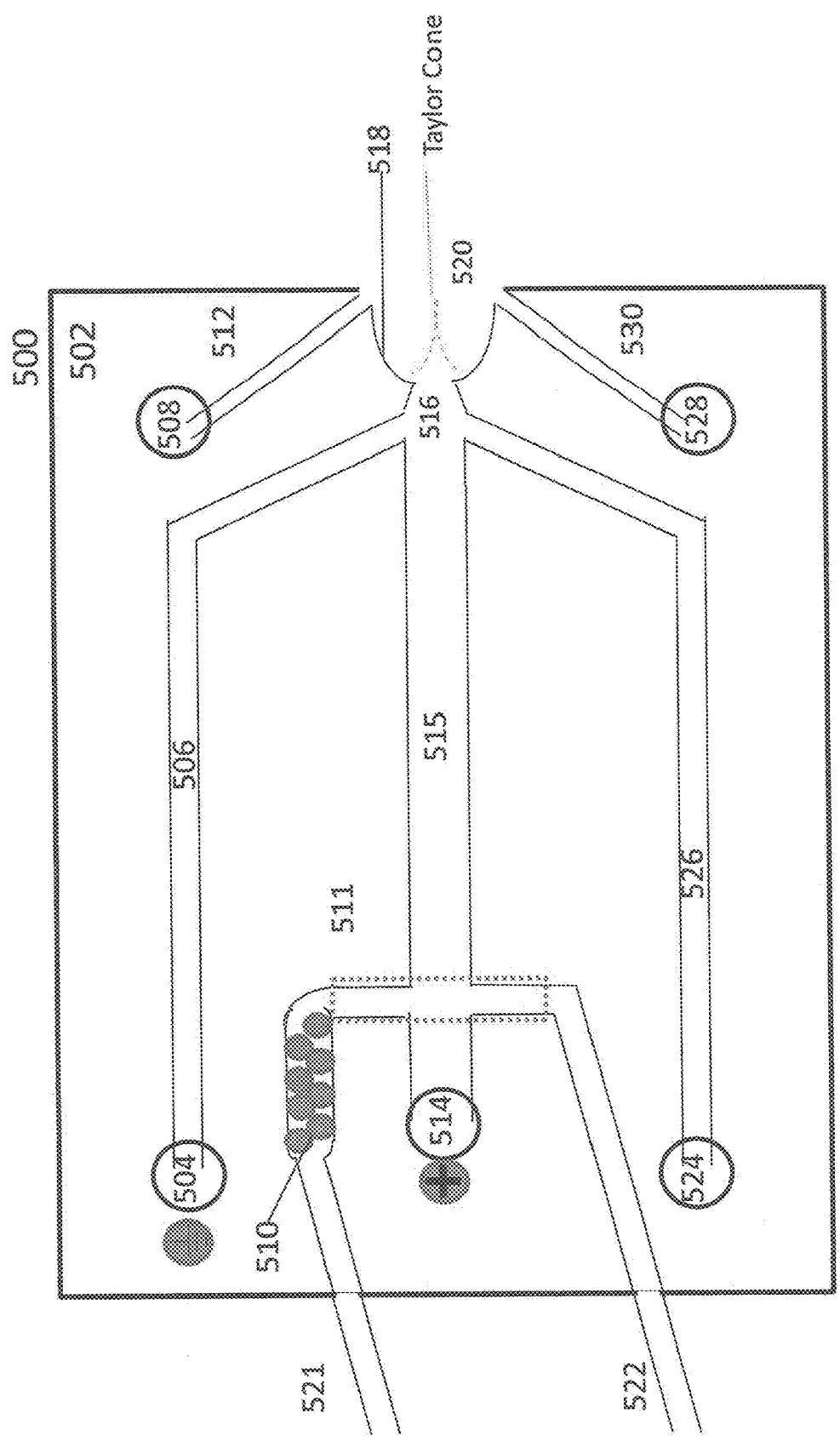
FIG. 5 is a schematic illustration of a microfluidic device, according to an embodiment.

Example 4 can be similar to example 2, but is described with reference to FIG. 5. A protein mixture can be loaded through inlet 521 and pass through to enrichment zone 510, which can contain beads derivatized with C18 for reversed-phase chromatography. During loading, fluid passes through the zone 510, through viewing region 511 and out outlet 522 to waste. Viewing region 510 transverses an internal layer made of soda-lime glass, which is opaque to 280 nm UV light, while the top and bottom layers are made of fused silica, which are transparent to 280 nm light.

A 280 nm light source is positioned below viewing region 511 and a CCD detector is placed above viewing region 511.

A solution of 20% $MeCN/H_2O$ is loaded through inlet 521 through enrichment zone 510. This solution will elute a fraction enriched for the least hydrophobic proteins in the mixture. Viewing region 511 is monitored for the absorbance of the enriched protein fraction at 280 nm as it moves from enrichment zone 510 to the outlet 522. When the fraction is positioned at the intersection of enrichment zone 510 and enrichment zone 515, a power supply is turned on creating an electric field between a positive electrode in reservoir 514 and ground at reservoir 504. This polarity can easily be reversed by switching the polarity of the power supply. Once the electric field is present, the enriched protein fraction will migrate down enrichment zone 515 separating proteins by capillary zone electrophoresis. The separated proteins will mix with the sheath, electrolyte solution at confluence 516, and form a Taylor cone on surface 518. Nebulizing Nitrogen gas line is connected to the device at ports 508 and 528, and moves through channels 512 and 530 to flank material from the electrospray as it exits the device via orifice 520.

Alternatively, hydrodynamic pressure could be used to load the enriched protein fraction into enrichment zone 515.

Example 5—Immunoprecipitation→Capillary Gel Electrophoresis of Protein Lysates

In this example, a microfluidic channel layer represented by the layout in FIG. 7 is fabricated from a cyclic olefin copolymer. Similarly stated, substrate 802 of microfluidic device 800 defines a channel network. For many applications, for example, if fluorescent detection is employed, microfluidic device 800 could be manufactured using a single material, provided that this material will transmit the wavelength range of light needed to detect the analyte.

Protein A coated beads are loaded into channel 806. These beads are rinsed with a solution of antibody raised against a target of interest, which will bind to the protein A beads. To reduce antibody shedding interfering with analyte detection, the antibody is then covalently cross-linked to the antibody to the bead using commercially available cross linking reagents, such as Dimethyl pimelimidate (DMP), Bis(sulfosuccinimidyl)suberate (BS3) and the like. After immunoprecipitation beads are prepared and loaded in channel 806, lysate analyte sample can be loaded via tube 804. After analyte is given sufficient time to be captured by immobilized antibody, unbound proteins are washed and cleared to waste via tube 822.

Next, the protein is eluted from the antibody beads so it can be analyzed. Elution is accomplished by loading solution of sodium dodecyl sulfate (SDS) and heating to 50 C for 10 minutes. Once released, the eluted analyte is flowed through channel 808 toward the intersection of channel 808 and 814. When the analyte plug reaches the intersection of channel 808 and 814, an electric field is turned on between a negative pole at reservoir 812 and a positive pole at reservoir 816, causing the negatively charged protein to migrate through a dextran linear polymer solution in channel 814, which has been loaded with the fluorogenic protein dye SYPRO® ruby.

Fluorescently labeled target protein can be visualized during CGE in channel 814 using whole column imaging. Similarly stated, the entirety of channel 814 can be imaged while the SYPRO® ruby dye is excited with 280 nm light and emitted light, at 618 nm, is measured by a detector.

Example 6—Variations of Microfluidic Design without Mass Spectrometer Interface

In some cases, it will be advantageous to have two designs of a microfluidic layer, that differ by presence or absence of the mass spectrometer interface. Once an analyte is characterized, confirmatory characterization may be done in the absence of the mass spectrometry data. By doing the confirmatory characterization in nearly the same microfluidic design, when an anomaly is identified, it will be simple to transfer the assay back to the chip with the mass spec interface for mass identification. This can eliminate the work otherwise needed to show that the anomaly in the confirmatory data is being analyzed in the mass spectrometry data.

Figure 8:
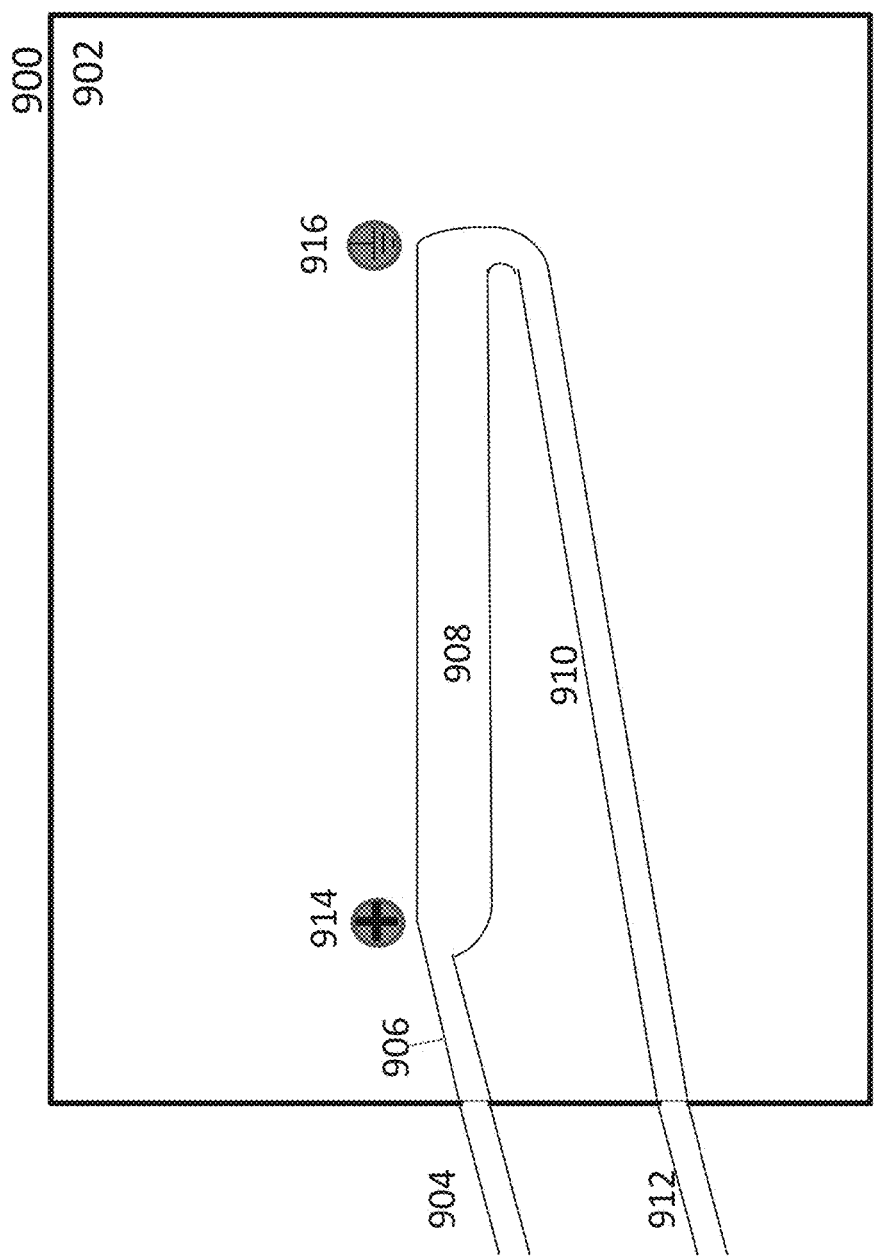
FIG. 8 is a schematic of a microfluidic device, according to an embodiment.

As an example, FIG. 8 shows a microfluidic design similar to microfluidic device 400 shown in FIG. 4, without orifice 424 and countersunk surface 422. Analyte is still introduced to the chip through an inlet 904 and channel 906 to an enrichment channel 908, but after analysis the sample will be flushed out through an outlet channel 910, rather than conducting electrospray ionization at an orifice. This design could be run for general operation, and then at times when mass identification is required, the same enrichment can be performed on the microfluidic device 400, shown in FIG. 4, ensuring identification of the analyte variants see on microfluidic device 900 of FIG. 8.

The foregoing descriptions of specific embodiments of the invention have been presented for purposes of illustration and description. They are not intended to be exhaustive or to limit the invention to the precise forms disclosed, and obviously many modifications and variations are possible in light of the above teaching. Although various embodiments have been described as having particular features and/or combinations of components, other embodiments are possible having a combination of any features and/or components from any of embodiments where appropriate. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially. While the embodiments have been particularly shown and described, it will be understood that various changes in form and details may be made.

All patents, patent applications, publications, and references cited herein are expressly incorporated by reference to the same extent as if each individual publication or patent application was specifically and individually indicated to be incorporated by reference.

What is claimed is:

1. A method, comprising:
in a microfluidic device, introducing an analyte mixture into a separation channel;
applying an electric field across the separation channel to effect a separation of the analyte mixture via isoelectric focusing;
continuously imaging the separation and mobilization of the analyte mixture by illuminating a first side of the microfluidic device through an optical slit, which provides optical access to the separation channel and detecting light passing through the optical slit and the separation channel;
introducing an electrolyte into a separated analyte mixture after the separation;
after introducing the electrolyte, expelling via electrospray ionization into a mass spectrometer substantially all of the analyte mixture from an orifice in line with the separation channel and in electrical communication with the separation channel's electric field; and
correlating absorbance peaks of separated analytes in the separation channel with data from the mass spectrometer of the separated analytes after the expelling of the separated analytes.

2. The method of claim 1, wherein the orifice is a recess on the microfluidic device, such that a Taylor cone formed by electrospray ionization is disposed entirely within the recess.

3. The method of claim 1, wherein the microfluidic device comprises a first separation channel and a second separation channel.

4. The method of claim 3, further comprising: chromatographically enriching the analyte mixture in the first separation channel before applying the electric field to effect the isoelectric focusing separation of the analyte mixture in the second separation channel.

5. The method of claim 1, wherein substantially all of the separated analyte mixture is expelled from the orifice in a continuous stream.

6. The method of claim 1, wherein:
the microfluidic device comprises a top layer, a middle layer, and a bottom layer;
the middle layer is constructed of an opaque substrate and the top layer and bottom layer are constructed of a transparent material; and
the separation channel defines the optical slit through the microfluidic device.

7. The method of claim 6, wherein the transparent material has a transmittance to allow ultraviolet (UV) light emitted by a light source positioned on one side of the microfluidic device to be quantified by a detector positioned on the other side of the microfluidic device.

8. The method of claim 7, wherein the transparent material has a transmissivity of at least 30%.

9. The method of claim 7, wherein the transparent material has a transmissivity of at least 50%.

10. The method of claim 7, wherein the transparent material has a transmissivity of at least 80%.

11. The method of claim 7, wherein the transparent material has a transmissivity of at least 95%.

12. The method of claim 1, further comprising introducing ampholytes into the separation channel before the separation of the analyte mixture to generate a pH gradient in the separation channel, introducing isoelectric point (pI) markers into the separation channel before the separation, and continuously imaging the separation channel while the pI markers are separated.

13. The method of claim 1, wherein the analyte mixture comprises intact proteins.

14. The method of claim 1, wherein the introducing of the electrolyte is performed by flowing an electrolyte solution from an electrolyte channel in fluid communication with a confluence region downstream of the separation channel.

15. The method of claim 1, wherein replenishment of ion potential occurs on the microfluidic device.

16. The method of claim 1, wherein the electrolyte is introduced by pressure.

17. The method of claim 1, wherein the electrolyte is introduced by electrophoresis.

18. The method of claim 14, wherein the microfluidic device is a cartridge comprising the separation channel, the orifice and the electrolyte introducing channel in static configuration.

19. The method of claim 18, wherein the separation channel and the electrolyte introducing channel intersect at a confluence region.

20. The method of claim 19, the confluence region is in the electric field of the separation channel.

21. The method of claim 19, wherein the confluence region is in line with the separation channel and the orifice.

22. The method of claim 1, wherein the microfluidic device comprises two electrodes generating an electric field across an electrolyte introducing channel.

23. The method of claim 18, wherein the cartridge further comprises an anolyte introducing channel and gas delivery channels for ionization.

* * * * *

UNITED STATES PATENT AND TRADEMARK OFFICE
CERTIFICATE OF CORRECTION

PATENT NO. : 10,209,217 B2
APPLICATION NO. : 15/709158
DATED : February 19, 2019
INVENTOR(S) : Erik Gentalen Page 1 of 1

It is certified that error appears in the above-identified patent and that said Letters Patent is hereby corrected as shown below:

In the Claims

Column 18, Line 39:
Please insert --,-- after "channel".

Signed and Sealed this
Thirtieth Day of April, 2019

Andrei Iancu
*Director of the United States Patent and Trademark Office*